United States Patent [19]

Rasmusson et al.

[11] 4,361,699
[45] Nov. 30, 1982

[54] NOVEL PROCESS FOR THE PREPARATION OF N[6]-ALKYL-ARPRINOCID

[75] Inventors: Gary H. Rasmusson, Watchung; Richard L. Tolman, Warren, both of N.J.

[73] Assignee: Merck & Co., Inc., Rahway, N.J.

[21] Appl. No.: 305,804

[22] Filed: Sep. 28, 1981

[51] Int. Cl.$^3$ .......................................... C07D 473/34
[52] U.S. Cl. .................................... 544/277; 424/253
[58] Field of Search ......................................... 544/277

[56] References Cited

U.S. PATENT DOCUMENTS 3,846,426  11/1974  Lira et al. .
4,189,485  2/1980   Matsuno et al. ................... 424/253

FOREIGN PATENT DOCUMENTS 1534163  11/1978  United Kingdom .

OTHER PUBLICATIONS

Meerwein et al., Ann. 641, 1, (1961).
Bredereck et al., Angew. Chem., 73, 493, (1961).
Neilson, Chemistry of Amidines and Imidates, Patai Ed., pp. 385-413, (1975).
Imai et al., European J. Med. Chems., 15, 207-210, (1980).

Primary Examiner—Mary C. Lee
Attorney, Agent, or Firm—David L. Rose; Mario A. Monaco

[57] ABSTRACT

This invention is concerned with a novel process for the preparation of N[6]-alkyl-arprinocid (6-alkyl-amino-9-substituted benzyl purines). Such compounds are active anticoccidial agents. The process involves the preparation of a Schiff base from an acetal of dialkylformamide and reduction with a metal hydride.

8 Claims, No Drawings

NOVEL PROCESS FOR THE PREPARATION OF N⁶-ALKYL-ARPRINOCID

BACKGROUND OF THE INVENTION

The use of 6-amino-9-substituted benzyl purines and the N⁶-alkyl derivatives thereof for the treatment of coccidiosis is well known (see U.S. Pat. No. 3,845,426 to Lira et al. issued 5 Nov. 1974 and Great Britain Pat. No. 1,534,163). In particular, the compound 6-amino-9(2-chloro-6-fluorobenzyl)purine is described as being particularly active and is sold under the generic name of arprinocid. The N⁶-alkyl derivatives of arprinocid have been prepared in low yields by the direct alkylation of arprinocid and using the more complicated procedures of aminolysis of 6-chloro-9-substituted benzyl purines or N'-alkylation of arprinocid followed by base catalyzed Dimroth rearrangement to the desired N⁶-alkyl-arprinocid. See the above British patent and the additional references of Wang et al. *Biochemical Pharmacology*, 28 2249–2260 (1979): K. Imai et al., *European Journal of Medicinal Chemistry*, 15 207–210 (1980). The instant procedure is an improvement over the prior art procedures in that the N⁶-alkyl-arprinocid is prepared in overall yields in excess of 90% in two steps.

SUMMARY OF THE INVENTION

The instant disclosure is concerned with the preparation of N⁶-alkyl-9-substituted benzyl purines which compounds are active anticoccidial agents. Thus, it is an object of this invention to disclose such a process. It is a further object to disclose reaction conditions for the optimum preparation of such compounds in an overall yield in excess of 90%. Further objects of this invention will become apparent from a reading of the following description.

DESCRIPTION OF THE INVENTION

The instant invention involves the preparation of N⁶-alkyl-arprinocid compounds from arprinocid in two steps with a marked improvement in yields over the prior art. The process is best illustrated in the following reaction scheme:

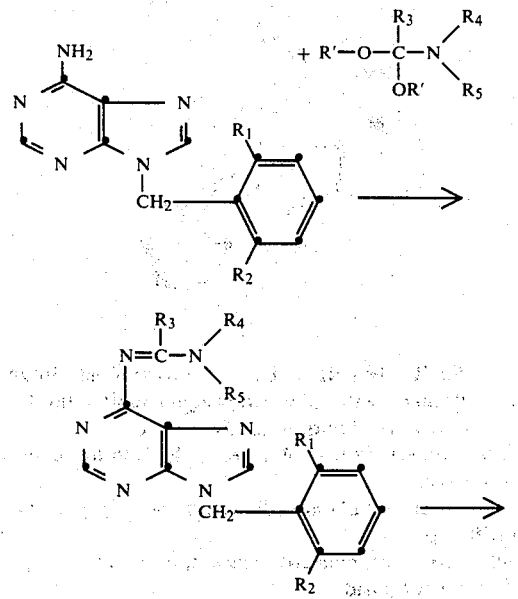

-continued

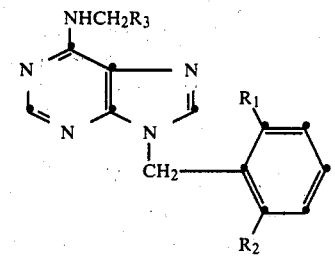

wherein $R_1$ and $R_2$ are halogen and $R_3$ is hydrogen or lower alkyl and $R_4$ and $R_5$ are loweralkyl.

It is preferred that $R_1$ be chlorine and R fluorine for optimum anticoccidial action of the final product, and that $R_3$ be hydrogen and $R_4$ and $R_5$ be methyl for optimum process yields.

In the instant disclosure, the term "lower alkyl" is intended to include those alkyl groups containing from 1–5 carbon atoms. Exemplary of such alkyl groups are methyl, ethyl, propyl, isopropyl, butyl, pentyl and the like.

The term "halogen" in the instant disclosure is intended to include the halogen atoms fluorine, chlorine, bromine and iodine.

The first step of the foregoing reaction scheme is carried out by mixing the two reactants neat or by dissolving them in a cosolvent. The reaction may be carried out equally well using either procedure, and the choice of whether to use a cosolvent or not depends more on the availability of the acetal of the aliphatic amide than upon the differences in reaction rates to be expected. If the aliphatic amide is relatively expensive, the choice would be to use a cosolvent. Where a cosolvent is to be employed, the preferred cosolvents are N,N-dimethylformamide, dimethylacetamide, (except in those cases where acetal exchange occurs), sulfolane, methylpyrrolidone, dimethylsulfoxide or hexamethylphosphoramide. The preferred solvents are N,N-dimethylformamide and dimethylsulfoxide. The reaction is preferably carried out at room temperature in order to maximize the yield and minimize the production of reaction by-products, however, if desired, the reaction may be carried out up to the boiling points of the reaction mixture. The reaction is generally complete in from one to 48 hours, however, most reactions are complete in about 24 hours. The desired product is isolated from the reaction mixture using techniques known to those skilled in the art.

The acetal reactant in the foregoing reaction scheme may be prepared using techniques described in the literature. References for the production of the above acetals of aliphatic amides by O-alkylation of an aliphatic tertiary amide to give a carbonium ion which is neutralized with alkoxide are Meerwein et al., *Ann.* 641, 1, (1961) and Bredereck et al., *Angen Chem*, 75, 493, (1961).

The resulting amidine derivative is reduced to the desired N-alkylarprinocid using a metal hydride preferably a metal borohydride and an aprotic solvent. The preferred metal borohydride is sodium borohydride. Other reducing agents that might be used are sodium cyanoborohydride, tetraalkylammonium borohydride, sulfurated sodium borohydride, lithium borohydride, potassium borohydride, calcium borohydride, zinc borohydride, trialkylamine borane and the like. The preferred solvents for the reaction are such dipolar solvents as dimethylsulfoxide, dioxane, sulfolane diglyme, triglyme and the like. The reaction is generally complete in from 1 to 90 minutes. The technique of sampling aliquots of the reaction mixture on thin layer chromatography plates to determine when the reaction is complete is very useful. The reaction mixture is generally heated to from 50° to 190° Celsius, however, it is preferred to maintain the reaction at about 100° C. until thin layer chromatography analysis indicates that the reaction is complete. The product is isolated using techniques know to those skilled in the art.

Coccidiosis is a wide-spread poultry disease which is produced by infections of protozoa of the genus Eimeria which causes severe pathology in the intestines and ceca of poultry. Some of the most significant of these species are E. tenella, E. acervulina, E. necatrix, E. brunetti and E. maxima. The disease is generally spread by the birds picking up the infectious organism in droppings on contaminated litter or ground or by way of food or drinking water. The disease is manifested by hemorrhage, accumulation of blood in the ceca, passage of blood in the droppings, weakness and digestive disturbances. The disease often terminated in the death of the animal but the fowl which survive severe infections have had their market value substantially reduced as a result of the infection. Coccidiosis is therefor a disease of great economic importance and extensive work has been done to find new and improved methods for controlling coccidial infections in poultry.

The following nonlimiting examples will serve to further illustrate the instant invention.

EXAMPLE 1
6-(N,N-dimethylaminomethylidineamino)-9-(2-chloro-6-fluorobenzyl)purine A mixture of 1.00 g of 6-amino-9-(2-chloro-6-fluorobenzyl)purine in 15 ml of dimethylformamidedimethylacetal is heated at 100° C. After 10 minutes, a solution forms which shortly thereafter starts producing a crystalline precipitate. The heating is continued for 2 hours. The thickened reaction mixture is then cooled in an ice bath and filtered. The solid is washed twice with 8 ml portions of ether. The solid material is dried in vacuo to give 1.139 g of 6-(N,N-dimethylaminomethylidineamino)-9-(2-chloro-6-fluorobenzyl)purine, melting point 172°-173° C.

EXAMPLE 2
$N^6$-methylarprinocid[6-methylamino-9-(2-chloro-6-fluorobenzyl)purine]

A mixture of 250 mg of 6-(N,N-dimethylaminomethylidineamino)-9-(2-chloro-6-fluorobenzyl)purine, 75 mg of sodium borohydride, 10 drops of methanol and 10 ml of dimethylsulfoxide are heated to 100° C. and maintained at that temperature for 1 hour. Thin layer chromatographic analysis indicates that the reaction is complete in 20 minutes. The reaction mixture is cooled in ice and treated with an equal volume of water. After cooling at 0° C., the precipitate is removed by filtration, washed with water and dried in air affording 155 mg of a crystalline solid with a melting point of 179°-181° C. The mother liquor is diluted with water and extracted with ethyl acette, the ethyl acetate extracts are washed twice with water, saturated sodium chloride solution, dried and evaporated to dryness affording 40 mg of a pale yellow crystalline product which upon recrystallization from 1.5 ml of isopropanol affords crystalline prisms that thin layer chromatographic analysis indicates to be equivalent in purity to the first crop and is identified as $N^6$-methylarprinocid.

What is claimed is:

1. A process for the preparation of a compound having a formula:

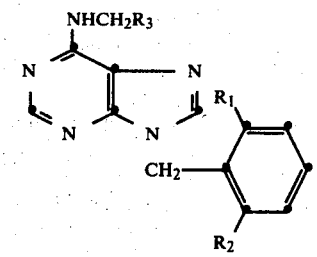

wherein $R_1$ and $R_2$ are halogen and $R_3$ is hydrogen or loweralkyl which comprises treating a compound having the formula:

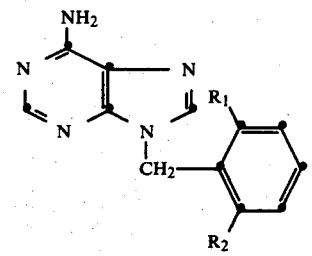

wherein $R_1$ and $R_2$ are as defined above with a compound having the formula:

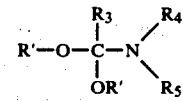

wherein $R_3$ is defined above and $R_4$ and $R_5$ are lower alkyl and $R''$ is lower alkyl, to prepare a compound having the formula:

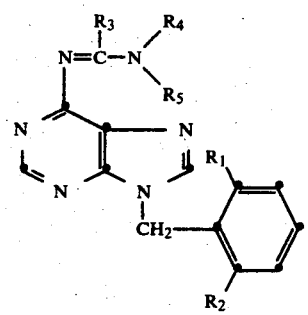

wherein $R_1$, $R_2$, $R_3$, $R_4$ and $R_5$ are as defined above which is treated with a reducing agent and a dipolar solvent to produce the desired compound.

2. The process of claim 1 wherein $R_1$ is chlorine and $R_2$ is fluorine.

3. The process of claim 1 wherein $R_3$ is hydrogen and $R_4$ and $R_5$ are methyl.

4. The process of claim 1 wherein the reducing agent is sodium borohydride.

5. A process for the preparation of the compound having the formula:

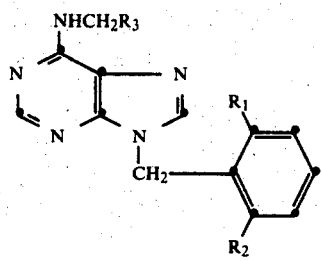

wherein $R_1$ and $R_2$ are halogen and $R_3$ is hydrogen or lower alkyl which comprises treating a compound having the formula:

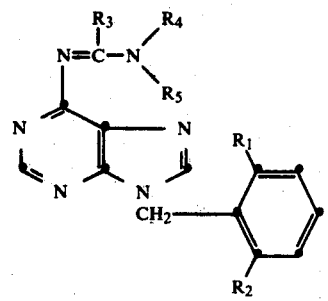

wherein $R_4$ and $R_5$ are lower alkyl, with a reducing agent in a dipolar solvent to produce the desired compound.

6. The process of claim 5 wherein $R_1$ is chlorine and $R_2$ is fluorine.

7. A process of claim 5 wherein $R_3$ is hydrogen and $R_4$ and $R_5$ are methyl.

8. A process of claim 5 wherein the reducing agent is sodium borohydride.

* * * * *